United States Patent [19]

Erdmann et al.

[11] Patent Number: 4,873,169

[45] Date of Patent: Oct. 10, 1989

[54] PROCESS FOR THE PREPARATION OF AN O-NAPHTHOQUINONEDIAZIDE SULFONIC ACID ESTER AND PHOTOSENSITIVE MIXTURE CONTAINING SAME

[75] Inventors: Fritz Erdmann, Eltville-Martinsthal; Horst-Dieter Thamm, Eschborn; Hans-Joachim Staudt, Taunusstein, all of Fed. Rep. of Germany

[73] Assignee: Hoechst Aktiengesellschaft, Frankfurt, Fed. Rep. of Germany

[21] Appl. No.: 87,599

[22] Filed: Aug. 20, 1987

[30] Foreign Application Priority Data

Aug. 27, 1986 [DE] Fed. Rep. of Germany ....... 3629122

[51] Int. Cl.[4] .......................... G03C 1/54; G03C 1/60; C07C 113/00
[52] U.S. Cl. ..................... 430/192; 430/165; 430/190; 430/193; 430/326; 534/556; 534/557
[58] Field of Search ............... 430/193, 192, 165, 190; 534/556, 557

[56] References Cited

U.S. PATENT DOCUMENTS

| | | | |
|---|---|---|---|
| 3,046,120 | 7/1962 | Schmidt et al. | 96/33 |
| 3,130,048 | 4/1964 | Fritz et al. | 96/33 |
| 3,647,443 | 3/1972 | Rauner et al. | 96/33 |
| 4,115,128 | 9/1978 | Kita | 96/91 D |
| 4,266,001 | 5/1981 | Buhr et al. | 430/192 |
| 4,275,139 | 6/1981 | Stahlhofen | 430/192 |
| 4,397,937 | 8/1983 | Clecak et al. | 430/192 |
| 4,424,270 | 1/1984 | Erdmann et al. | 430/166 |
| 4,610,953 | 9/1986 | Hashimoto et al. | 430/331 |
| 4,681,923 | 7/1987 | Demmer et al. | 430/190 |

FOREIGN PATENT DOCUMENTS

| | | | |
|---|---|---|---|
| 1113759 | 5/1968 | United Kingdom | 430/192 |
| 1330932 | 9/1973 | United Kingdom | 430/192 |

*Primary Examiner*—Charles L. Bowers, Jr.
*Attorney, Agent, or Firm*—Foley & Lardner, Schwartz, Jeffery, Schwaab, Mack, Blumenthal & Evans

[57] ABSTRACT

A process for the preparation of an o-naphthoquinonediazide sulfonic acid ester is disclosed. Esterification of an o-naphthoquinonediazide sulfonic acid halide with a mono- or polyvalent phenolic compound in a solvent is performed in the presence of ammonia, of ammonium salts of weak acids or of aliphatic derivatives of ammonia having 1 to 3 carbon atoms, at a pH within the range from about 1.5 to about 8.5 and a temperature within the range from about 15° C. to about 40° C. The esters of o-naphthoquinonediazide sulfonic acid which are obtained by this process contain only small amounts of metal ions and can be used in photosensitive mixtures satisfying high requirements of the microelectronics industry.

18 Claims, No Drawings

PROCESS FOR THE PREPARATION OF AN O-NAPHTHOQUINONEDIAZIDE SULFONIC ACID ESTER AND PHOTOSENSITIVE MIXTURE CONTAINING SAME

BACKGROUND OF THE INVENTION

The present invention relates to the preparation of an o-naphthoquinonediazide sulfonic acid ester. More particularly, it relates to a process for esterifying an o-naphthoquinonediazide sulfonic acid halide, in particular chloride, with a mono- or polyvalent phenolic compound, in a solvent in the presence of a basic component, followed by precipitation of the ester and drying. The invention also relates to the use of the ester in a photosensitive mixture.

German Pat. No. 865,860 (equivalent to U.S. Pat. No. 3,046,120) discloses that photosensitive components, which are suitable as basic materials for copying layers, can be obtained from reaction products of o-naphthoquinonediazide sulfonic acid halides with alkali-soluble phenol/formaldehyde resins.

In general, the esterification reaction between the o-naphthoquinonediazide sulfonic acid halide and the phenolic compound is conducted in a polar organic solvent, for example, dioxane, acetone, methyl-ethyl ketone, or in a solvent mixture, in a way such that inorganic bases, for example, alkali carbonates, alkali bicarbonates, alkaline-earth carbonates, and the like, are added to the reaction mixture in molar ratios as an acid-binding, basic component.

When the reaction is completed, the reaction products can be isolated from the mixture in various ways, for example, by precipitation with a non-polar solvent or by the addition of water. Due to the process of preparation employed, the resulting products still contain small amounts of the metal ions used for the condensation reaction, and therefore they cannot be used without reservation.

German Auslegungsschrift No. 20 44 868 (equivalent to U.S. Pat. No. 3,647,443) discloses the reaction of o-naphthoquinonediazide sulfonyl chloride with phenolic components in solvents, such as pyridine, picoline, lutidine, or triethylamine. The reaction can be performed under standard conditions and at reduced or elevated temperatures. The reaction products are isolated by neutralizing the reaction mixture with a diluted acid, for example, hydrochloric acid, followed by extraction with the aid of a halogenated hydrocarbon solvent, for example, methylene chloride.

Apart from the use of bases which in some cases present toxic hazards, this process has the disadvantage that a residual portion of alkaline hydrochlorides remains in the reaction product. During the working-up of the reaction products, these residuals may cause discolorations or, in the course of the preparation of photosensitive systems from the products, lead to damage to the sensitive processing equipment by corrosion. Another disadvantage resides in the high technical expenditure which is necessary to remove the remaining alkaline hydrochlorides from the reaction product.

With the increasing scale of integration, the esters of o-naphthoquinonediazide sulfonic acid and the photosensitive positive-working reproduction layers prepared from them, for example, for applications in the field of printed circuit technology and especially for the patterning of silicon surfaces in the field of microelectronics, have to satisfy continuously increasing requirements. In this respect, one of the most stringent requirements is the exclusion of metal ions in the reaction product.

The main requirements concern the absence of ions in the photosensitive mixtures. Particularly disturbing are metal ions, for example, Na, K, Mg, Mn, Fe, Bi, Sb, As, Cu, Cr, Ni, Zn, Se ions, because these either act as so-called doping elements or adversely affect the behavior during the subsequent etching step by causing irregularities in the crystal lattice of the silicon surface.

SUMMARY OF THE INVENTION

It is therefore an object of the present invention to provide a process for the preparation of o-naphthoquinone diazide sulfonic acid esters, which avoids the described disavantages and satisfies the continuously growing demands of the microelectronics industry.

It is a further object of the invention to provide a process for preparing o-naphthoquinone diazide sulfonic acid esters which are essentially metal ion free.

It is another object of the invention to provide a process for preparing o-naphthoquinone diazide sulfonic acid esters which does not present toxic hazards.

It is yet another object of the present invention to provide a process for preparing o-naphthoquinone diazide sulfonic acid esters which have no discoloring or corrosive residuals.

It is a further object of the invention to provide a photosensitive material containing an o-naphthoquinone diazide sulfonic acid ester which is metal ion free, noncorrosive, and not subject to discoloration.

In accomplishing these and other objects of the invention, there has been provided a process in which the esterification is performed in the presence of ammonia, of ammonium salts of weak acids or of monohydroxy aliphatic amine with 1 to 3 carbon atoms or dihydroxy aliphatic amine with 1 to 3 carbon atoms, at a pH within the range from about 1.5 to about 8.5 and at a temperature within the range from about 15° C. to about 40° C. Preferably, the esterification is performed in the presence of aqueous ammonia, ammonium salts of carboxylic or acetic acid or in the presence of mono- or diethanolamine. The preferred pH is in the range from about 6 to 8 and the preferred temperature is in the range from about 20° C. to about 35° C.

This process ensures that the undesirable impurities of the o-naphthoquinonediazide sulfonic acid esters are reduced to an indispensible minimum or are completely eliminated. By means of the process of this invention, the desired products are obtained in high-purity qualities and high yields.

DESCRIPTION OF THE PREFERRED EMBODIMENTS

The process according to the present invention comprises reacting an o-naphthoquinonediazide sulfonic acid halide, in particular the corresponding chloride, with a phenolic compound, in a way such that the components are dissolved in polar organic solvents or solvent mixtures and are then allowed to react in the presence of a basic component, optionally with the addition of water. The temperature and pH must be controlled carefully.

The course of the reaction, which results in the desired o-naphthoquinonediazide sulfonic acid ester, is surprising. Because of the nucleophilic character of the co-reactants avaiable to the sulfonyl halide, it could be expected that the hydrolysis reaction resulting in the free sulfonic acid or, respectively, the reaction with the amine resulting in the corresponding sulfonic acid amine would be predominant.

Apart from the excellent water-solubility of the resulting alkaline hydrochlorides, which makes it easy to separate them from the end products by washing out, the process of this invention in particular presents the advantage that the ammonium chloride which forms when ammonia is used is thermally unstable and therefore can be completely removed without difficulty during the drying stage.

The resulting products fulfil all requirements that photosensitive systems which are to be used in the field of microelectronics must meet.

In order to avoid discolorations and to suppress side-reactions it is important to run the condensation reaction with exact temperature and pH control.

Suitable ammonium salts of weak acids include salts of carbonic acid, such as ammonium carbonate or ammonium bicarbonate, which in the course of the reaction are converted into easily soluble and volatile constituents which can be removed during the drying process at the latest, and salts of a carboxylic acid, such as ammonium acetate.

Suitable monohydroxy aliphatic amines with 1 to 3 carbon atoms or dihydroxy aliphatic amines with 1 to 3 carbon atoms are primary amines having 1 to 3 carbon atoms, which can carry further substituents. Particular preference is given to monoethanolamine and diethanolamine.

The chlorides, which are known per se are preferred among the o-naphthoquinonediazide sulfonic acid halides. Principally, it is, however, also possible to employ the bromides, which are likewise known. The compounds are derived from the naphthoquinone-(1,2)-diazide, in particular from the -diazide-(2). The compounds can contain one or two sulfonyl halide groups in their molecules, which sulfonyl halide groups can be present in the 3-, 4-, 5-, 6-, 7- or 8-position of the naphthalene nucleus. Of the monosulfonic acids, the 4-sulfonic acid and, preferably, the 5-sulfonic acid are employed in most instances. If disulfonic acids are used, the sulfonic acid groups can, for example, be present in the 3,5-; 3,6-; 4,6- or in the 5,7-position.

Suitable mono- or polyvalent phenolic compounds preferably include low-molecular weight phenols. It is also possible to use polymeric compounds possessing phenolic hydroxy groups or mixtures thereof.

Preferably employed low-molecular weight phenols are compounds having at least two benzene nuclei in their molecules, which contain at least two phenolic hydroxy groups.

A preferred group of phenolic compounds is represented by the general formula

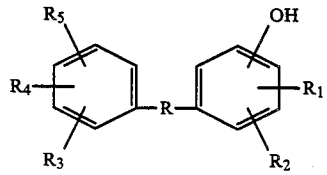

in which

R denotes a single bond or one of the groups CO, S, O, $SO_2$ or $CR_6R_7$, preferably CO or $CR_6R_7$, $R_1$, $R_2$, $R_3$ denote hydrogen or halogen atoms, $R_4$ and $R_5$ hydroxy groups, or alkyl or alkoxy groups having 1 to 4 carbon atoms, and $R_6$ and $R_7$ denote hydrogen atoms or alkyl groups having 1 to 4 carbon atoms, preferably hydrogen atoms or methyl groups, or in which two of the radicals $R_3$, $R_4$ and $R_5$ and the radicals $R_1$ und $R_2$ together each denote an aromatic ring, whereby in all cases at least one of the radicals $R_1$, $R_2$, $R_3$, $R_4$ and $R_5$ denotes a hydroxy group.

Examples of suitable low-molecular weight phenolic compounds include 2,4-dihydroxy-benzophenone, 2,3,4-trihydroxy-benzophenone, 2,4,2',4'-tetrahydroxydiphenyl-sulfide, 2,2'-dihydroxy-dinaphthyl-methane, 4,4'-dihydroxy-2,2'-dimethyl-5,5'-di-tert.-butyl-diphenyl-sulfide, 4,4'-dihydroxy-diphenyl-sulfide, 4,6-bis-(2,4-dihydroxy-phenylthio)resorcinol, 2,4,2',4'-tetrahydroxy-3,5,3',5'-tetrabromodiphenylsulfone, 2,4,2',4'-tetrahydroxy-3,5,3',5'-tetrabromodiphenyl or 2,4-dihydroxy-3,5-dibromo-benzophenone.

Suitable polymeric comounds with phenolic hydroxy groups above all include condensation resins of phenols and carbonyl compounds. Preferred reactants are condensation products which themselves are known as customary constituents of o-naphthoquinonediazide layers. For this reason particular preference is given to phenol/formaldehyde novolaks or cresol/formaldehyde novolaks. The use of the esterification products of these resins has the added advantage that a certain content of unesterified phenolic compound does not cause any nuisance, for it is a constituent part of the mixture anyhow. Further suitable phenolic resins are condensation products of pyrogallol and acetone, as described in British Pat. No. 1,113,759, incorporated herein by reference. It is also possible to employ the polycondensation products obtained from polyhydroxybenzophenones and formaldehyde which are described in German Offenlegungsschrift No. 28 47 878, incorporated herein by reference.

In general, the o-naphthoquinonediazide sulfonic acid chloride and the phenolic compound are dissolved at room temperature in a suitable solvent, and the base required for the condensation reaction, which is preferably dissolved in water, is then slowly measured in, such that the temperature of the reaction mixture is adjusted to about 15° C. to 40° C., and the pH is kept within the range from about 1.5 to 8.5, preferably from 6 to 8. When the addition of the base is completed, the mixture is stirred for another 0.5 to 10 minutes and worked up.

The resulting product is separated off, repeatedly washed with water and dried. In this form it can be directly employed for the preparation of photosensitive mixtures.

Therefore, the present invention also relates to a photosensitive mixture containing a binder which is insoluble in water and soluble in aqueous-alkaline solutions and comprises the ester prepared in accordance with this invention.

Film-forming phenolic resins having a molecular weight between about 300 and 5,000 are used as binders. They are obtained by condensing phenol or substituted phenol with formaldehyde. Suitable substituted phenols include cresol, xylenol, butylphenol, and the like. Among the alkali-soluble, film-forming phenolic resins, phenol/formaldehyde novolaks, cresol/formaldehyde novolaks and phenol-modified xylenol/formaldehyde novolaks are particularly preferred. The amount of phenolic resin varies between about 50 and 90% by weight, preferably about 65 to 85% by weight, of the total non-volatile constituents.

The mixtures of this invention may contain conventionally employed fillers, dyes, pigments, photolytic acid formers, for example, 1,2-naphthoquinonediazide-(2)-4-sulfonic acid chloride, and other known additives and auxiliaries.

The support material is coated in a manner well-known from the art, for example, by spraying or casting. The applied layer suitably has a dry weight of 1.0 to 3.0 g/m².

The invention will be explained in greater detail by means of the Examples which follow.

EXAMPLE 1

28.8 p.b.w. (parts by weight) of naphthoquinone-(1,2)-diazide-(2)-5-sulfonyl chloride and
17.6 p.b.w. of 2,3,4-trihydroxybenzophenone are disolved in
161 p.b.w. of acetone, and then
8.6 p.b.w. of an aqueous 25% by weight strength ammonia solution
are added to the resulting acetone solution of the first-mentioned reactants. The pH and temperature are controlled, such that the temperature varies between about 15° C. and 35° C. and the pH is kept within the range from about 2 to 7.5.

When the addition is completed, stirring is continued for another 5 minutes, then the pH is adjusted to a value of less than 2 by means of hydrochloric acid, and the reaction solution is poured into
1,000 p.b.w. of fully deionized water.

The resulting precipitate is removed in known manner by suction, using a vacuum filter. By careful washing with about
3,000 p.b.w. of fully deionized water
the ammonium chloride, which is readily soluble in water, can be washed out completely. The filtrate is controlled by measuring its conductivity, and the precipitate is washed until the conductivity of the filtrate is equal to or less than about 10 μS.

Then the precipitate is dried, so that 40 b.p.w. of a mixture of the mono-, bis- and triesters of the above-listed starting compounds are obtained, which can be directly used in ion-free microelectronics resists.

EXAMPLE 2

22 p.b.w. of naphthoquinone-(1,2)-diazide-(2)-5-sulfonyl chloride and
17.6 p.b.w. of 2,3,4-trihydroxybenzophenone are disolved in
161 p.b.w. of acetone, and then
6.6 p.b.w. of monoethanolamine
are added to the resulting acetone solution of the first-mentioned reactants. The pH and temperature are controlled, such that the temperature varies between about 15° C. and 35° C. and the pH is kept within the range from about 2 to 7.5.

When the addition is completed, stirring is continued for another 5 minutes, then the pH is adjusted to a value of less than 2 by means of hydrochloric acid, and the reaction solution is poured into
1,600 p.b.w. of fully deionized water.

The resulting precipitate is removed by suction, using a vacuum filter. By careful washing with about
3,000 p.b.w. of fully deionized water
the alkaline chloride, which is readily soluble can be washed out completely. The electric conductivity of the purifying water is measured as described in Example 1.

Then the precipitate is dried, so that
33 p.b.w. of a mixture of the mono-, bis- and triesters of the above-listed starting compounds,
are obtained which can be directly used in metal ion-free electronics resists.

EXAMPLE 3

22 p.b.w. of naphthoquinone-(1,2)-diazide-(2)-5-sulfonyl chloride and
17.6 p.b.w. of 2,3,4-trihydroxybenzophenone are disolved in
167 p.b.w. of acetone, and then
23.5 p.b.w. of an aqueous 35% by weight strength ammonium acetate solution
are added to the resulting acetone solution of the first-mentioned reactants. The pH and temperature are controlled, such that the temperature varies between about 15° C. and 35° C. and the pH is kept within the range from about 2 to 7.5.

When the addition is completed, stirring is continued for another 5 minutes, then the pH is adjusted to a value of less than 2 by means of hydrochloric acid, and the reaction solution is poured into
1,600 p.b.w. of fully deionized water.

The resulting precipitate is removed by suction, using a vacuum filter. By careful washing with about
3,000 p.b.w. of fully deionized water
the ammonium chloride, which is readily soluble, can be washed out completely.

Then the precipitate is dried, so that
31 p.b.w. of a mixture of the mono-, bis- and triesters of the above-listed starting compounds
are obtained, which can be used directly in metal ion-free liquid resists.

COMPARATIVE EXAMPLE 25 p.b.w. of a polymer of the novolak type (softening point 112° C. to 119° C., content of phenolic groups 14% by weight)
are dissolved, at room temperature and with stirring, in
68 p.b.w. of a mixture of ethyl glycol acetate, acetic acid butyl ester and xylene (80:10:10).

The resulting solution is mixed with
7 p.b.w. of a quinonediazide compound, prepared in accordance with German Pat. No. 865,860 (equivalent to U.S. Pat. No. 3,046,120),
and the mixture is stirred until all constituents are dissolved.

The solution is further processed by filtering as desribed above, so that a positive-working, ready-for-use photoresist having the following metal ion concentration is obtained:
55 ppm of $Na^+$ ions; 2.9 ppm of $Fe^{++}/^{+++}$ ions; and 1.5 ppm of $Ca^{++}$ ions.

The individual concentrations are measured by means of atomic absorption spectroscopy (AAS).

EXAMPLE 4

25 p.b.w. of a polymer of the novolak type, as described in the Comparative Example above,
are dissolved, at room temperature, in
68 p.b.w. of a solvent mixture as described in the Comparative Example.

The resulting solution is mixed with
7 p.b.w. of a naphthoquinonediazide sulfonic acid ester mixture as described in Example 1.

The mixture is stirred until all constituents are dissolved.

The solution is further processed as described above, so that a positive-working, ready-for-use photoresist having the following metal ion concentration is obtained:

$Na^+$: less than 1 ppm; $Fe^{++}/^{+++}$: less than 1 ppm, $K^+$, $Mg^+$, $Ca^{++}$, $Cu^{++}$ and $Mn^{++}$: each time less than 1 ppm.

What is claimed is:

1. A process for the preparation of an o-naphthoquinone diazide sulfonic acid ester comprising the steps of:
    mixing an o-naphthoquinone diazide sulfonic acid halide with a mono- or polyvalent phenolic compound in a solvent;
    adding a basic component selected from the group consisting of ammonia, ammonium salts of weak acids and monohydroxy aliphatic amine with 1 to 3 carbon atoms or dihydroxy aliphatic amine with 1 to 3 carbon atoms;
    controlling the pH within the range from about 1.5 to about 8.5 and the temperature within the range from about 15° C. to about 40° C. to carry out an esterification reaction producing an o-naphthoquinone diazide sulfonic acid ester; and
    precipitating the o-naphthoquinone diazide sulfonic acid ester produced.

2. An o-naphthoquinoe diazide sulfonic acid ester having less than about 1 p.p.m. of any metal ion, prepared by the process according to claim 1.

3. A photosensitive mixture comprising a photosensitive o-naphthoquinone diazide sulfonic acid ester prepared by the process according to claim 1 in admixture with from about 50 to 90% of a binder which is insoluble in water and soluble in aqueous-alkaline solutions.

4. A process as claimed in claim 1, wherein the esterification is performed in the presence of aqueous ammonia.

5. A process as claimed in claim 1, wherein the esterification is performed in the presence of ammonium salts of a carbonic or carboxylic acid.

6. A process as claimed in claim 1, wherein the esterification is performed in the presence of monoethanolamine or diethanolamine.

7. A process as claimed in claim 1, wherein the esterification is performed at a pH within the range from about 6 to about 8.

8. A process as claimed in claim 1, wherein the esterification is performed at a temperature within the range from about 20° C. to about 35° C.

9. A process as claimed in claim 5, wherein the carboxylic acid comprises acetic acid.

10. A process as claimed in claim 1, wherein the phenolic compound is a low molecular weight phenol having at least two benzene nuclei and at least two phenolic hydroxy groups.

11. A process as claimed in claim 1, wherein the phenolic compound is represented by the formula

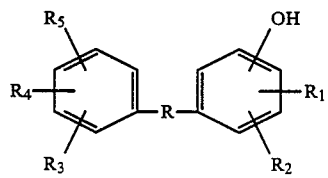

in which
    R denotes a single bond or one of the groups CO, S, O, $SO_2$ or $CR_6R_7$, preferably CO or $CR_6R_7$,
    $R_1$, $R_2$, $R_3$ denote hydrogen or halogen atoms,
    $R_4$ and $R_5$ denote hydroxy groups, or alkyl or alkoxy groups having 1 to 4 carbon atoms, and
    $R_6$ and $R_7$ denote hydrogen atoms or alkyl groups having 1 to 4 carbon atoms, preferably hydrogen atoms or methyl groups,
or in which two of the radicals $R_3$, $R_4$ and $R_5$ and the radicals $R_1$ und $R_2$ together each denote an aromatic ring, whereby in all cases at least one of the radicals $R_1$, $R_2$, $R_3$, $R_4$ and $R_5$ denotes a hydroxy group.

12. A process as claimed in claim 1, wherein the o-naphthoquinone diazide sulfonic acid halide comprises a chloride.

13. A process as claimed in claim 1, wherein the phenolic compound comprises at least one polymeric compound having phenolic hydroxy groups.

14. A process as claimed in claim 13, wherein the polymeric compound comprises a condensation resin of a phenol and a carbonyl compound.

15. A process as claimed in claim 13, wherein the condensation resin is selected from the group consisting of cresol/formaldehyde and phenol/formaldehyde.

16. A process as claimed in claim 14, wherein the condensation resin is selected from the group consisting of pyrogallol/acetone and polyhydroxybenzophenone/formaldehyde.

17. A process as claimed in claim 1, wherein easily-separated, water-soluble alkaline hydrochlorides are produced during said esterification reaction.

18. A process as claimed in claim 1, consisting essentially of the recited steps.

* * * * *